United States Patent [19]

Farrar et al.

[11] Patent Number: 5,888,494
[45] Date of Patent: Mar. 30, 1999

[54] FILM-FORMING COMPOSITIONS OF ANTIHYPERALGESIC OPIATES AND METHOD OF TREATING HYPERALGESIC AND PRURITIC CONDITIONS THEREWITH

[75] Inventors: John J. Farrar, Chester Springs; Alan L. Maycock, Malvern; Virendra Kumar, Paoli; Imre Jim Balogh, Perkasie, all of Pa.

[73] Assignee: Adolor Corporation, Malvern, Pa.

[21] Appl. No.: 891,924

[22] Filed: Jul. 14, 1997

Related U.S. Application Data

[63] Continuation-in-part of Ser. No. 614,027, Mar. 12, 1996, Pat. No. 5,667,773.

[51] Int. Cl.⁶ ............... A61K 31/00; A61K 9/08; A61K 7/40; A61K 31/445
[52] U.S. Cl. ................... 424/78.05; 424/78.06; 424/78.07
[58] Field of Search ............ 424/78.02, 78.03, 424/78.05, 78.06

[56] References Cited

U.S. PATENT DOCUMENTS

| | | |
|---|---|---|
| 3,714,159 | 1/1973 | Janssen et al. . |
| 3,884,916 | 5/1975 | Janssen et al. . |
| 3,996,214 | 12/1976 | Dajani et al. . |
| 4,012,393 | 3/1977 | Markos et al. . |
| 4,025,652 | 5/1977 | Diamond et al. . |
| 4,060,635 | 11/1977 | Diamond et al. . |
| 4,103,668 | 8/1978 | Adelstein et al. . |
| 4,115,564 | 9/1978 | Diamond et al. . |
| 4,203,920 | 5/1980 | Diamond et al. . |
| 4,326,074 | 4/1982 | Diamond et al. . |
| 4,326,075 | 4/1982 | Diamond et al. . |
| 4,533,739 | 8/1985 | Pitzele et al. . |
| 4,623,539 | 11/1986 | Tunc ................................ 424/78.01 |
| 4,946,870 | 8/1990 | Partain, III et al. . |
| 5,236,947 | 8/1993 | Calvet et al. . |
| 5,242,944 | 9/1993 | Park et al. . |
| 5,258,436 | 11/1993 | Wheatley et al. . |
| 5,348,744 | 9/1994 | Kurazumi et al. . |
| 5,576,346 | 11/1996 | Clemente et al. ............. 514/456 |
| 5,667,773 | 9/1997 | Farrar et al. .................. 424/78.05 |

FOREIGN PATENT DOCUMENTS

| | | | |
|---|---|---|---|
| 2636559 | 3/1977 | Germany ................. 424/78.02 |
| 933668 | 8/1963 | United Kingdom ........ 424/78.02 |

OTHER PUBLICATIONS

McMahon et al., TINS, vol. 15, No. 12 (1992).
Bernstein et al., Journal of Investigative Dermatology, 78:82–83 (1982).
Ballantyne et al., Pain, 33: 149–160 (1988).
J. D. Bernhard, J. Am. Acad. Derm. 24:309 (1991).
IASP Newsletter, Sep./Oct. 1996.
Thomas et al., Brain Research, 695: 267–270 (1995).

*Primary Examiner*—Peter F. Kulkosky
*Attorney, Agent, or Firm*—Imre Balogh

[57] ABSTRACT

Topical film-forming compositions for the prevention and treatment of prutitus containing an opiate that is substantially devoid of central nervous system effects.

1 Claim, No Drawings

FILM-FORMING COMPOSITIONS OF ANTIHYPERALGESIC OPIATES AND METHOD OF TREATING HYPERALGESIC AND PRURITIC CONDITIONS THEREWITH

This application is a continuation-in-part of application Ser. No. 08/614,027, filed on Mar. 12,1996, now U.S. Pat No. 5,667,773.

BACKGROUND OF THE INVENTION

1. Field of the Invention

This invention relates to film-forming compositions of anti-hyperalgesic opiates having substantially no effects on the central nervous system and method of topically treating hyperalgesic conditions.

The present invention also relates to compositions and methods for the prevention and/or treatment of itch, also known as prutitus, which has many causes. The compositions which are formulated for topical administration contain antihyperalgesic opiates that are substantially devoid of central nervous system effects, and, thus, have very little, if any potential for producing side effects with centrally acting antihyperalgesic opiates.

2. Reported Developments

A) Antihyperalgesic Opiates

Pain is the effect of noxious stimuli on nerve endings of a subject which results in the transmission of impulses to the cerebrum. This sensation informs the subject of actual or impending tissue damage and elicits a defensive response. The degree of response substantially correlates with the degree of noxious stimuli in order to speedily avoid further tissue damage and to re-establish normal pre-injury conditions in the subject. The sensation of pain, however, does not end with the stoppage of the noxious stimuli but continues to persist during the inflammation stage of the injury. In turn, the continuation of pain perception causes discomfort to, and deleteriously affects the well-being of, the subject. It is, therefore, important to reduce and/or eliminate pain perception of a subject subsequent to injuries.

The reduction/elimination of pain perception can be affected by the central nervous system (hereinafter sometimes referred to as CNS)-mediated analgesia which leads to an overall inhibition of the pain transmission. CNS-mediated analgesia can be effected by systemically administered opiates which, by interaction with specific receptors in the brain and spinal cord, are able to block pain transmission. Systemic opiates, such as morphine, which have been used for many years to control post injury pain, have side effects because their actions within the brain include sedation, depression of respiration, constipation, nausea and development of addiction and dependence. When peripherally applied, opiates have a short duration of action and still possess the undesirable side effects.

Certain opiates, such as loperamide [i.e., 4-(p-chlorophenyl)-4-hydroxy-N-N-dimethyl-α,α-diphenyl-1-piperidinebutyramide hydrochloride] and its analogs were reported to be devoid of CNS effects, which is believed to be due to the failure of the opiates to cross the blood brain barrier. Loperamide HCl has been used for a long time in antidiarrheal formulations and has been completely free of the undesirable CNS effects. It would be desirable to use such opiates to inhibit/eliminate post-injury pain without concomitant CNS effects.

The present invention provides safe and effective topical film-forming compositions for inhibiting/eliminating the sensation of pain.

B) Antihyperalgesic Opiates as Anti-Pruritic Agents

The prior art has investigated the physiology and treatment of prutitus as illustrated hereunder.

Itch is a well known sensory state associated with the desire to scratch. As with pain, itch can be produced by a variety of chemical, mechanical, thermal or electrical stimuli. In addition to the difference in the sensory quality of itch and pain, they also differ in that (1) itch, unlike pain, can only be evoked from the superficial layers of skin, mucosa, and conjunctiva, and (2) itch and pain usually do not occur simultaneously from the same skin region; in fact, mildly painful stimuli, such as scratching, are effective in eliminating itch. In addition, the application of histamine to skin produces itch but not pain. Itch and pain are further dissociated pharmacologically: itch appears to be insensitive to opiate and non-steroidal anti-inflammatory drug (NSAID) treatment, both of which are effective in treating pain.

Although itch and pain are of a class in that both are modalities of nociception transmitted by small unmyelinated C fibers, evidence that itch is not just a variety of low-threshold pain is overwhelming. Itch leads to the reflex or urge to scratch; pain leads to withdrawal Removal of the epidermis eliminates itch but causes pain. Analgesics, particularly opiods, relieve pain but often cause itch (see, for example *J. Am. Acad. Derm.* 24: 309–310, 1991). There can be no doubt that itching is of eminent clinical importance; many systemic and skin diseases are accompanied by persistent or recurrent itch attacks. Current knowledge suggests that itch has several features in common with pain but exhibits intriguing differences as well (see, for example, W. Magerl, *IASP Newsletter,* pp. 4–7, Sept/Oct 1996).

McMahon et al (*TINS*, Vol. 15, No. 12, pp. 497–501, 1992) provides a description of stimuli (Table a) and a comparison of the established features of itch and pain (Table b):

TABLE a

Stimuli that can elicit or augment itch

Physical

Mechanical. Light touch, pressure, suction.
Thermal. Warming.
Electrical. Focal transcutaneous repetitive stimulation, transcutaneous constant current stimulation, intraneural microstimulation.
Chemical Non-specific irritants. Acids, alkalis.
Inflammatory mediators. Histamine, kallikrein, bradykinin, prostaglandins.
Histamine-releasing substances. Compound 48/80, protamine, C3a.
Peptidases. Mucunain, papain, trypsin, mast cell chymase.
Neuropeptides. Substance P, vasoactive intestinal polypeptide, neurotensin, secretin.
Opioids. Morphine, β-endorphin, enkephalin analogues.

TABLE b

Comparison of the established features of itch and pain

| | ITCH | PAIN |
|---|---|---|
| Psychophysiology | | |
| Tissue | Skin. Mucous membranes | Most tissues |
| Stimulus | See Table a | Many stimuli |
| Intraneural microstimulation | Occasionally | Yes |
| Secondary sensations | Alloknesis (itchy skin) | Hyperalgesia |

TABLE b-continued

Comparison of the established features of itch and pain

|  | ITCH | PAIN |
| --- | --- | --- |
| Psychogenic modification | Pronounced | Present |
| Counterstimuli | Scratching, pain, cooling | Tactile stimuli, cooling |
| Neurophysiology |  |  |
| Primary afferent neurones | C- and Aδ-fibres | C- and Aδ-fibres |
| Flare size | Large | Small |
| Spinal pathway | Anterolateral funiculus | Anterolateral funiculus |
| Protective reflexes | Scratching, sneezing | Flexion, guarding |
| Autonomic reflexes | Yes | Yes |
| Pharmacology |  |  |
| Capsaicin sensitivity | Yes | Chemogenic pain; yes |
| NSAID sensitivity | Probably not | Yes |
| Morphine sensitivity | No | Yes |

Abbreviation: NSAID, non-steroidal anti-inflammatory drugs.

Experimental focal itch stimuli are surrounded by a halo of seemingly unaffected tissue where light tactile stimuli are capable of eliciting itch-like sensations. The term itchy skin or alloknesis has been coined for these secondary sensations that are reminiscent of the features of secondary hyperalgesia evolving around a painful focus. A crucial observation is that itch and pain usually do not coexist in the same skin region and a mild noxious stimulus such as scratching is in fact the singly most effective way to abolish itch. This abolition of itch can be prolonged producing an 'antipruritic state'. Although mild scratch is often not painful, microneurographic recordings from humans have directly determined that such stimuli are among the most effective ways to excite cutaneous unmyelinated nociceptive afferents. (See, for example:

Shelly, W. B. and Arthur, R. P. (1957) *Arch. Dernatol.* 76, 296–323;

Simone, D. A. et al. (1987) *Somatosens. Res.* 5, 81–92;

Graham, D. T. , Goodell, H. and Wolff, H. G. (1951) *J. Clin. Invest.* 30, 37–49;

Simone, D. A., Alreja, M. and LaMotte, R. H. (1991) *Somatosens, Mot. Res.* 8, 271–279;

Torebjörk, E (1985) *Philos. Trans. R. Soc. London Ser.* B 308, 227–234; and

Vallbo, A. B., Hagbarth, K. E., Torebjörk, H. E. and Wallin, B. G. (1979) *Physiol. Rev.* 59,919–957).

Physiologically, there is evidence that substance P released from nociceptor terminals can cause the release of histamine from mast cells. Activation of mast cells, with release of the pruritogen histamine, occurs in immediate type hypersensitivity diseases, such as anaphylactic reactions and urticaria. Urticarial eruptions are distinctly pruritic and can involve any portion of the body, and have a variety of causes beyond hypersensitivity, including physical stimuli such as cold, solar radiation, exercise and mechanical irritation. Other causes of prutitus include: chiggers, the larval form of which secretes substance that creates a red papule that itches intensely; secondary hyperparathyroidism associated with chronic renal failure; cutaneous larva migrans, caused by burrowing larvae of animal hookworms; dermal myiasis, caused by maggots of the horse botfly, which can afflict horseback riders; onchocerciasis ("river blindness") caused by filarial nematodes; pediculosis, caused by lice infestations; enterobiasis (pinworm) infestations, which afflict about 40 million Americans, particularly school children; schistosome dermatitis (swimmer's itch); psoriasis; poison ivy; and asteatotic eczema ("winter itch"). The role of histamine or other endogenous pruritogens in mediating itch associated with these and other pruritic conditions, such as atopic dermatitis, its not yet well established. For atopic dermatitis, in particular, it appears that itch is not inhibited by antihistamines, but by cyclosporin A, a drug which inhibits the production of cytokines which have been proposed as potential pruritogens.

Current therapies for the treatment of itch include a variety of topical and systemic agents, such as steroids, antihistamines, and some psychotherapeutic tricyclic compounds, such as doxepin hydrochloride. Many such agents are listed in PDR *Generics* (see Second Edition, 1996, p. cv for a listing of said agents). The limitations of these agents are well known to medical practitioners, and are summarized in the "Warnings" and "Precautions" sections for the individual agents listed in PDR *Generics*. In particular, the lack of complete efficacy of antihistamines is well known, but antihistamines are frequently used in dermatology to treat prutitus due to urticaria, atopic dermatitis, contact dermatitis, psoriasis, and a variety of other conditions. Although sedation has been a frequent side effect of conventional systemically administered antihistamines, a new generation of antihistamines have been developed that are nonsedating, apparently due to their inability to cross the blood-brain barrier.

Intravenous administration of opiate analgesics, such as morphine and hydromorphone has been associated with prutitus, urticaria, other skin rashes, and wheal and flare over the vein being injected. These itch and itch-related reactions are believed to be due to a histamine-releasing property of these opiates, via mast cell degranulation. These opiates are thought to act upon the mu subtype of opiate receptor, but the possibility of interactions at the other principal opiate receptor subtypes (delta and kappa) cannot be excluded since these and other pruritogenic analgesics are not pure mu agonists. The cellular loci of the receptor type(s) mediating the itching effect is not known, although the mast cell is a possible candidate since opiates cause histamine release from these cells. However, some investigators have suggested that the frequent inability of antihistamines to block morphine-induced itching suggests a non-histaminergic mediation of opiate-induced itching—mechanism which could involve central opiate receptors. Although i.v. morphine only occasionally results in general itching (in about 1% of patients), prutitus is more prevalent in opiate analgesia with epidural (8.5%) or intraspinal (45.8%) administration. (See, for example: Bernstein et al., "Antipruritic Effect of an Opiate Antagonist, Naloxone Hydrochloride", *The Journal of Investigative Dermatology,* 78:82–83, 1982; and Ballantyne et al., "Itching after epidural and spinal opiates", *Pain,* 33: 149–160, 1988.)

To date, treatment with opiates has not only proven useless in the treatment of itch, but appears to exacerbate itch in mammals. The consistent findings from human studies indicate that whether by central or peripheral mechanisms, opiates appear to promote rather than prevent itching, and that opiate antagonists have antipuritic activity.

Human clinical studies have generally shown that opiates cause itching and there is evidence that these effects can be reproduced in animal models, where itching sensations per se cannot be reported, but scratching behavior can be observed. (See, for example: Thomas et al., "Microinjection of morphine into the rat medullary dorsal horn produces a dose-dependent increase in facial-scratching", *Brain Research*, 695: 267–270, 1996; Thomas et al., "Effects of central administration of opioids on facial scratching in monkeys", *Brain Res.*, 585: 315–317, 1992; and Thomas et al., "The medullary dorsal horn: A site of action of opioids in producing facial scratching in monkeys", *Anesthesiology*, 79: 548–554, 1993).

We have now discovered that certain opiates, which are substantially devoid of central nervous system effects, in topical film-forming formulations possess anti-pruritic activity in addition to antihyperalgesic activity. Accordingly, the present invention also provides safe and effective film-forming compositions for the prevention and treatment of prutitus.

SUMMARY OF THE INVENTION

The present invention provides a topical anti-hyperalgesic/anti-pruritic composition comprising:

(a) from about 1.0 to about 65% w/w of an anti-hyperalgesic/anti-pruritic compound incorporated in a film-forming polymeric material;

(b) said film-forming polymeric material being present in said composition of from about 1 to about 76% w/w and is capable of forming an essentially continuous film in the pH environment of from about 5.5 to about 8.5, said polymeric material having atoms containing polarizable electrons thereon, said atoms being selected from the group consisting of oxygen, nitrogen, sulfur in combination with a divalent cation, said divalent cation is selected from the group consisting of $Ca^{++}$, $Mg^{++}$, $Zn^{++}$ and $Ba^{++}$ wherein the ratio of said atoms containing polarizable electrons thereon to said divalent cations is in the range of from about 7.7 to about 1; and (c) of from about 23 to about 34% w/w of an aqueous pharmaceutically acceptable carrier.

In another aspect the present invention provides: (1) a method for the inhibition of post-injury pain associated with local inflammatory conditions including inflammation following infection, blisters, boils, acute skin injuries, abrasions, burns, cuts, contusions, surgical incisions, irritations from various sources, poison ivy, allergic rashes, dermatitis, stings and bites and inflammation of joints by depositing the topical composition onto the site of the condition where the sensation of pain occurs; and (2) a method for the prevention or treatment of prutitus.

The methods (1) and (2) comprise topically administering an effective amount of said film-forming composition to a patient to inhibit/eliminate pain or to prevent or treat prutitus.

DETAILED DESCRIPTION OF THE INVENTION

The Anti-Hyperalgesic Compounds

The compounds for use in the compositions and methods herein possess peripheral anti-hyperalgesic and substantially no CNS activities because they do not cross the blood brain barrier. The failure to cross the blood brain barrier precludes the occurrence of the CNS systemic side effects, so that there is no potential for abuse. The compounds intended for use in the methods and compositions provided herein include any compound that by virtue of its interaction, either directly or indirectly, with peripheral opioid receptors ameliorates the peripheral hyperalgesic state, but does not exhibit systemic CNS-mediated analgesic activity or CNS side effects, including heaviness of the limbs, flush or pale complexion, clogged nasal and sinus passages, dizziness, depression, respiratory depression, sedation and constipation. These compounds include antidiarrheals that act as antidiarrheals via interaction, with $\mu$, $\delta$, or $\kappa$ receptors, and opiate agonists, such as metkephamide and related enkephalin analogs. The compounds of the present invention, the description of which follows, have been reported in prior art patents all of which are incorporated herein by reference:

(a) Loperamide, its analogs, and its related compounds, metabolites and prodrugs thereof reported in U.S. Pat. Nos.

| | |
|---|---|
| 3,714,159 | 4,125,531 |
| 3,884,916 | 4,194,045 |
| 3,996,214 | 4,203,920 |
| 4,012,393 | 4,277,605 |
| 4,013,668 | 4,326,074 |
| 4,025,652 | 4,326,075 |
| 4,060,635 | 4,533,739 |
| 4,066,654 | 4,824,853 |
| 4,069,223 | 4,990,521 |
| 4,072,686 | 5,236,947 |
| 4,115,564 | 5,242,944 |
| 4,116,963 | |

Such compounds include compounds of Formula I; its N-oxide or a pharmaceutically acceptable salt or acid:

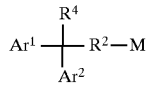

wherein M is

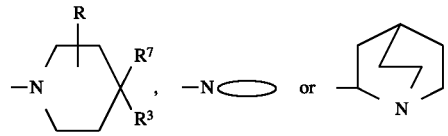

wherein:

is an azabicycloalkyl containing from 6 to 9 carbon atoms with at least 5 atoms in each ring and is unsubstituted or substituted with $OR^{18}$ in which $R^{18}$ is hydrogen or lower alkanoyl containing 2 to 7 carbons and $OR^{18}$ is at the 5 position in 5-membered rings or the 5 or 6 position in 6-membered rings and is attached in the endo or exo configuration;

$Ar^1$ and $Ar^2$ are either (i) or (ii) as follows:

(i) each is independently selected from aryl and heteroaryl groups containing from 5 to 7 members in the ring, each is unsubstituted or substituted with one or more substituents selected from halo, haloalkyl, hydroxy, alkyl, alkyloxy, aminosulfonyl, alkylcarbonyl, nitro, haloalkyl, trifluoromethyl, amino, aminocarbonyl, phenylcarbonyl or thienyl, where the alkyl groups are straight or branched chains lower alkyl containing from 1 to 6 carbon atoms; or (ii) $Ar^1$ and $Ar^2$ are each independently phenyl or pyridyl groups and with the carbon to which they are commonly linked form a fused ring so that the compounds of formula (1) have the structure:

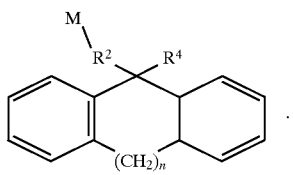

wherein n is 0 to 3;

$R^2$ is either alkyl in which the alkyl group is a straight or branched chain having 1 to 12 carbon atoms, or is alkylene having 1 to 6 carbon atoms with one or two double bonds;

$R^3$ is $Ar^3$, —Y—$Ar^3$, where Y is alkylene or alkyl having 1 to 3 carbon atoms, or is

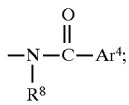

$R^8$ is hydrogen or alkyl that is a straight or branched chain containing from 1 to 6 carbon atoms;

$Ar^3$ is aryl or heteroaryl containing from 5 to 7 members in the ring, which is unsubstituted or substituted with one or more substituents of halo, halo lower alkyl or lower alkyl;

$Ar^4$ is either:
(i) is a heterocycle containing one to three fused rings or which is unsubstituted or substituted with one or more substituents selected from halo, halo lower alkyl or lower alkyl, or
(ii) $Ar^4$ is a radical of formula:

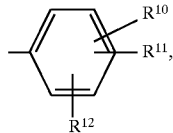

in which $R^{10}$, $R^{11}$ and $R^{12}$ are each independently selected from hydrogen, alkyl, alkyloxy, alkoxyalkyl, halo, haloalkyl, hydroxy, cyano, nitro, amino, alkylamino, di(alkyl)amino, aminocarbonyl, arylcarbonylamino, alkylcarbonylamino, alkylcarbonyl alkylcarbonyloxy, aminosulfonyl, alkylsulfinyl, alkylsulfonyl, alkylthio, mercapto, $C_3$–$C_6$ alkenyloxy, arylalkyloxy, aryloxy or alkyl, in which each group is unsubstituted or substituted with one or more halo atoms, halo alkyl or alkyl, and the alkyl groups are straight or branched chains that are lower alkyl;

R is hydrogen, alkyl, halo, haloalkyl or $OR^9$;

$R^9$ is selected from alkyl arylalkyl, alkylcarbonyl, aminoalkyl, alkylaminoalkyl or dialkylaminoalkyl in which the alkyl groups are straight or branched chains containing 1 to 12 carbon atoms;

$R^4$ is selected from among:
(i) 5- to 7-membered aryl groups, which are unsubstituted or substituted with lower alkyl, halo lower alkyl or halo, or
(ii) heterocyclic rings, containing one to three heteroatoms, that are unsubstituted or substituted with halo, halo lower alkyl or lower alkyl, or
(iii) alkyl containing from 1 to 8 carbon atoms, alkenyl containing 3 to 6 carbon atoms, cycloalkyl containing from 3 to 6 carbon atoms, cycloalkyl alkyl in which the first alkyl contains 3 to 6 carbons and the second containing 1 to 3 carbons, or cycloalkenyl containing 4 to 7 carbons, or

where $R^5$ and $R^6$ are either:
(i) independently selected from hydrogen, alkyl, which is a straight or branched chain containing 1 to 12 carbon atoms, alkenyl which is straight or branched chain, containing 1 to 12 carbon atoms and one or two double bonds, or aryl which contains 5 to 7 carbon atoms, or
(ii) $R^5$ and $R^6$ are selected from carbon chains, heteroatoms, and carbon chains containing one or more heteroatoms, so that with the nitrogen atoms to which each is attached they form a 3- to 7-membered heterocyclic ring containing one to three heteroatoms that is unsubstituted or substituted with halo, halo lower alkyl or lower alkyl; and $R^7$ is selected from among:
H;
OH;
—$R^{14}OR^{13}$ in which $R^{13}$ is hydrogen or lower alkyl, alkanoyl containing 2 to 5 carbon atoms, and $R^{14}$ is lower alkenyl or lower alkyl;
—$CH_2NR^{15}R^{16}$ in which $R^{15}$ is hydrogen, lower alkyl or lower alkanoyl and $R^{16}$ is hydrogen or lower alkyl;
$OR^{15}$;
$R^{22}OR^{13}$, in which $R^{22}$ is lower alkyl;
—C(O)$OR^{17}$ in which $R^{17}$ is hydrogen, alkyl containing form 1 to 7 carbons or alkenyl having 3–7 carbon atoms, aryl or heteroaryl; or an alkali metal or alkaline earth metal salt.

The nomenclatures are to be understood to have the meaning generally understood by those skilled in the art as defined herein:

"Halogen" or "halide" or "halo" refers to F, Cl, Br or I, and also pseudohalides. In preferred embodiments halo refers to F, Cl, Br and I.

Pseudohalides are radicals that behave substantially similar to halides. Such radicals can be used in the same manner and treated in the same manner as halides (X, in which X is a halogen, such as Cl or Br). Pseudohalides include, but are not limited to cyanide, cyanate, thiocyanate, selenocyanate, azide and trifluoromethyl. As used herein, carbon chains and carbon chains with heteroatoms may be straight or branched or, if they contain 3 or more members, may be cyclic.

Alkyl alkenyl and alkynyl carbon chains, if not specified contain from 1 to 20 carbons, preferably 1 to 12 carbons and are straight or branched.

Lower alkyl lower alkenyl, and lower alkynyl refer to carbon chains having one to about 6 carbons. In preferred embodiments of the compounds provided herein that includes alkyl alkenyl, or alkynyl portions include lower alkyl, lower alkenyl and lower alkynyl portions. Preferred among lower carbon chains are those having 1–3 carbons.

Aryl refers to cyclic groups containing from 3 to 15 or 16 carbon atoms, preferably from 5 to 10, more preferably 5 to 7 carbons. Aryl groups include, but are not limited to, groups such as phenyl, substituted phenyl naphthyl, substituted naphthyl, in which the substituent is lower alkyl, halo, halo lower alkyl, or lower alkoxy. Preferred aryl groups are lower aryl groups that contain less than 7 carbons in the ring structure.

Cycloalkyl refers to saturated cyclic carbon chains; cycloalkyenyl and cycloalkynyl refer to cyclic carbon chains that include at least one unsaturated triple bond. The cyclic portions of the carbon chains may include one ring or two or more fused rings.

Carbocyclic group is a ring containing at least three carbons; a heterocyclic group is a ring containing at least one carbon and one or more heteroatoms, preferably selected from among O, S and N, more preferably N and O. A heteroaryl group is an unsaturated ring structure containing 1 or more, preferably 1 to 3 heteroatoms in the ring. The rings may be single or two or more fused rings. Heteroaryl is used interchangeably with heterocycle.

Heterocycle refers to ring structures that include at least one carbon atom and one or more atoms, such as N, S, and O.

Alkyl refers to non-aromatic carbon chains that contain one or more carbons; the chains may be straight or branched or include cyclic portions or be cyclic.

Alicyclic refers to aryl groups that are cyclic.

Haloalkyl refers to an alkyl radical, preferably lower alkyl, in which one or more of the hydrogen atoms are replaced by halogen including, but not limited to, chloromethyl trifluoromethyl 1-chloro-2-fluoroethyl and other such groups. Halo lower alkyl refers to lower alkyl substituted with one or more halo substituents, and is preferably trichloromethyl or trifluoromethyl.

Haloalkoxy refers to RO— in which R is a haloalkyl group.

Aminocarbonyl refers to —C(O)NH$_2$.

Alkylaminocarbonyl refers to —C(O)NHR in which R is hydrogen, alkyl, preferably lower alkyl or aryl, preferably lower aryl.

Dialkylamincarbonyl refers to —C(O)NR'R in which R' and R are independently selected from alkyl or aryl preferably lower alkyl or lower aryl; carboxamide: refers to groups of formula NR' COR.

Alkoxycarbonyl as used herein refers to —C(O)OR in which R is alkyl, preferably lower alkyl or aryl, preferably lower aryl.

Alkoxy and thioalkoxy refer to RO— and RS—, in which R is alkyl, preferably lower alkyl or aryl, preferably lower aryl.

When a particular group, such as phenyl or pyridyl is specified, this means that the group is unsubstituted or is substituted.

The compounds can be made as described in the above-cited and herein incorporated patents of which the following are preferred.

2-[4(4-hydroxy-4-phenylpiperidino)-2,2-diphenylbutyryl]-piperidine;
4-{4-[4-hydroxy-4-(3-trifluoromethylphenyl)piperidino]-2,2-diphenylbutyryl}morpholine;
1-{4-[4-hydroxy-4-(3-trifluoromethylphenyl)-piperidino]-2,2-diphenylbutyl}piperidine;
4-(p-chlorophenyl)-4-hydroxy-N-N-trimethyl-α,α-diphenylpiperidine-1-butyramide;
4-(p-chlorophenyl)-4-hydroxy-N-N-dimethyl-α,α-diphenylpiperidine-1-butyramide[loperamide];
4-(p-chlorophenyl)-4-hydroxy-N-N-dimethyl-α,α-diphenylpiperidine-1-N-oxide-butyramide[loperamide];
4-(3,4-dichlorophenyl)-N-N-diethyl-4-hydroxy-α,α-diphenylpiperidine-1-butyramide;
4-(3,4-dichlorophenyl)-4-hydroxy-N-N-dimethyl-α,α-diphenylpiperidine-1-butyramide;
4-(4-chloro-3-trifluoromethylphenyl)-4-hydroxy-N-N-dimethyl-α,α-diphenylpiperidine-1-butyramide;
4-(p-fluorophenyl)-4-hydroxy-N-N-trimethyl-α,α-diphenylpiperidine-1-butyramide;
4-(p-bromophenyl)-4-hydroxy-N-N-dimethyl-α,α-diphenylpiperdine-1-butyramide;
1-{4-[4-(3,4-dichlorophenyl)-4-hydroxypiperidino]-2,2-diphenylbutyryl}pyrrolidine;
4-(p-chlorophenyl)-N-ethyl-4-hydroxy-N-methyl-α,α-diphenylpiperidine-1-butyramide;
5-[1,1-diphenyl-3-(exo-5-hydroxy-2-azabicyclo[2,2.-2]oct-2-yl)-propyl]-2-methyl-1,3,4-oxadiazole;
5-[1,1-diphenyl-3-(exo-5-acetoxy-2-azabicyclo[2.2.-2]oct-2-yl)-propyl]-2-methyl-1,3,4-oxadiazole;
5-[1,1-diphenyl-3-(endo-5-acetoxy-2-azabicyclo[2.2.-2]oct-2-yl)-propyl]-2-methyl-1,3,4-oxadiazole;
5-[1,1-diphenyl-3-(endo-5-hydroxy-2-azabicyclo[2.2.-2]oct-2-yl)-propyl]-2-methyl-1,3,4-oxadiazole;
5-[1,1-diphenyl-3-(end-6-acetoxy-2-azabicyclo[2.2.-2]oct-2-yl)-propyl]-2-methyl-1,3,4-oxadiazole;
5-[1,1-diphenyl-3-(endo-6-hydroxy-2-azabicyclo[2.2.-2]oct-2-yl)-propyl]-2-methyl-1,3,4-oxadiazole;
5-[1,1-diphenyl-3-(exo-6-acetoxy-2-azabicyclo[2.2.-2]oct-2-yl)-propyl]-2-methyl 1,3,4-oxadiazole;
5-[1,1-diphenyl-3-(exo-6-hydroxy-2-azabicyclo[2.2.-2]oct-2-yl)-propyl]-2-methyl-1,3,4-oxadiazole;
1-(3,3,3-triphenylpropyl)-4-phenyl-4-piperidinecarboxylic acid hydrochloride;
ethyl 1-(3,3,3-triphenylpropyl)-4-phenyl-4-piperidinecarboxylate;
potassium 1-(3,3,3-triphenylpropyl)-4-phenyl-4-piperidinecarboxylate;
sodium 1-(3,3,3-triphenylpropyl)-4-phenyl-4-piperidinecarboxylate;
1-[3,3-diphenyl-3-(2-pyridyl)propyl]-4-phenyl-4-piperidinecarboxylic acid hydrochloride;
sodium 1-[3,3-diphenyl-3-(2-pyridyl)propyl]-4-phenyl-4-piperidinecarboxylate;
ethyl 1-[3,3-diphenyl-3-(2-pyridyl)propyl]-4-phenyl-4-piperidinecarboxylate;
potassium 1-[3,3-diphenyl-3-(2-pyridyl)propyl]-4-phenyl-4-piperidinecarboxylate;
1-(3,3,3-triphenylpropyl)-4-phenyl-4-piperidinemethanol;
1-[3,3-diphenyl-3-(2-pyridyl)propyl-4-phenyl-4-piperidinemethanol;
1-(3,3,3-triphenylpropyl)-4-phenyl-4-acetoxymethyl-piperidine;
1-(3,3,3-triphenylpropyl)-4-phenyl-4-methoxymethyl-piperidine;
1-(3,3,3-triphenylpropyl)-4-(4-chlorophenyl)-4-piperidinemethanol;
1-[3-(p-chlorophenyl)-3,3-diphenylpropyl]-4-(phenyl)-4-piperidinemethanol;
1-[3-(p-tolyl)-3,3-diphenylpropyl]4(phenyl)-4-piperidinemethanol;
1-[3-(p-bromophenyl)-3,3-diphenylpropyl]-4-(phenyl)-4-piperidinemethanol;
1-[3,3-diphenyl-3-(4-pyridyl)-propyl]-4-phenyl-4-piperidinemethanol;
1-[3,3-diphenyl-3-(3-pyridyl)propyl]-4-phenyl-4-piperidinemethanol;
1-(3,3,3-triphenylpropyl)-4-phenyl-4-hexoxymethyl-piperidine;
1-(3,3,3-triphenylpropyl)-4-(p-tolyl)-4-piperidinemethanol;
1-(3,3,3-triphenylpropyl)-4-(p-trifluoromethyl)-4-piperidinemethanol;
1-(3,3,3-triphenylbutyl)-4-(phenyl)-4-piperidinemethanol;

1-(3,3,3-triphenylpropyl)-4-(phenyl)-4-piperidinemethanol;
1-(3,3,3-triphenylpropyl)-4-(phenyl)-4-methoxyethylpiperidine;
1-[3,3-diphenyl-3-(2-pyridyl)propyl]-4-phenyl-4-methoxyethylpiperidine;
1-(3,3,3-triphenylpropyl)-4-phenyl-4-piperidinemethanol;
1-[3,3-diphenyl-3-(2-pyridyl)propyl]-4-phenyl-4-piperidinemethanol;
1-(3,3,3-triphenylpropyl)-4-phenyl-4-acetoxymethylpiperidine;
1-(3,3,3-triphenylpropyl)-4-phenyl-4-methoxymethylpiperidine;
1-(3,3,3-triphenylpropyl)-4-(chlorophenyl)-4-piperidinemethanol;
1-(3,3,3-tiphenylpropyl)-4-hydroxy-4-benzylpiperidine and 1-(3,3,3-triphenylpropyl)-4-hydroxy-4-benzylpiperidine; hydrochloride;
1-(3,3,3-tiphenylpropyl)-4-hydroxy-4-(p-chlorobenzyl) piperidine;
1-(3,3,3-triphenylpropyl)-4-hydroxy-4-(p-methylbenzyl) piperidine;
1-[3,3,3(2-pyridyl)propyl]-4-benzyl-4-hydroxypiperidine;
m-chlorophenylamidinourea;
p-chlorophenylamidinourea;
3,4-dichlorophenylamidinourea;
m-bromophenylamidinourea;
p-bromophenylamidinourea;
3,4-dibromo-phenylamidinourea;
3-chloro-4-bromophenylamidinourea;
3-bromo-chlorophenylamidinourea;
3-chloro-4-fluorophenylamidinourea;
3-bromo-4-fluorophenylamidinourea;
3-fluoro-4-chlorophenylamidinourea;
2,6-dimethylphenylamidinourea;
2,6-diethylphenylamidinourea;
2-methyl-6-ethylphenylamidinourea;
2-methyl-6-methoxyphenylamidinourea;
2-methyl-6-ethoxyphenylamidinourea;
2-ethyl-6-methoxyphenylamidinourea;
2-ethyl-6-ethoxyphenylamidinourea;
3,4-dimethoxyphenylamidinourea;
3,4-dihydroxyphenylamidinourea;
3,4,5-trimethoxyphenylamidinourea;
3,4,5-trihydroxyphenylamidinourea;
2-[(2-methyl-3-aminophenyl)amino]-1-pyrroline, dihydrochloride;
2-[(2-methyl-3-acetamidophenyl)amino]-1-pyrroline, hydrochloride;
2-[(2-methyl-3-(ethoxycarbonylamino)phenyl-)amino]-1-pyrroline, hydrochloride;
2-(2,2-diphenylpentyl)-1-azabicylo[2.2.2]octane;
2-(2,2-diphenylhexyl)-1-azabicylo[2.2.2]octane;
2-(2,2-diphenylpropyl)-1-azabicylo[2.2.2]octane;
2-(2,2-diphenyloctyl)-1-azabicylo[2.2.2]octane; and
2-(2,2-diphenylheptyl)-1-azabicylo[2.2.2]octane.

Of these compounds, loperamide, [4-(p-chlorophenyl)-4-hydroxy-N-N-dimethyl -α,α-diphenyl-1-piperidenebutyramide monochloride]

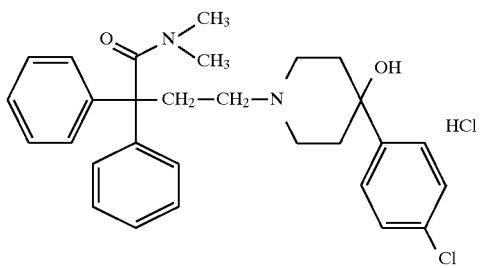

and the N-oxides of loperamide.

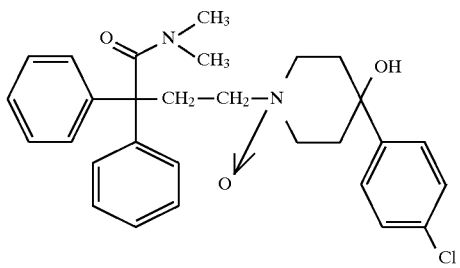

are most preferred.

The Film-Forming Polymers

The film forming polymeric materials used in the present invention are described in U.S. Pat. No. 4,623,539 which is incorporated herein by reference. The film-forming materials are non-toxic, and contain no leachable components which would deleteriously affect the site of injury. The materials form a film or coating in the pH range of from about 5.5 to about 8.5 which adheres to the site of injury and delivers the anti-hyperalgesic compounds contained therein.

Broadly defined, the polymers capable of forming such films include certain anionic, cationic and neutral polymers.

I. Anionic Polymers

These polymers carry negative charges when in the ionized form. The anionic polymers bind to the cell surfaces and to protein molecules of the cells. The major forces responsible for these interactions are electrostatic in nature.

Suitable anionic polymers are represented by the generalized formulas:

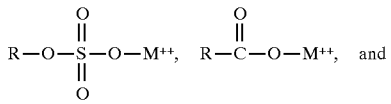

wherein R represents the polymeric chain or residue;

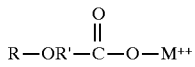

represent anionic ligands; and $M^{++}$ represents a divalent cation.

Specific anionic polymers useful in the present invention include:

A. sulfated polysaccharides;
B. carboxylated polysaccharides;

C. cellulose derivatives; and
D. sulfated, sulfonated or carboxylated synthetic polymers.

A. Sulfated Polysaccharides

Polysaccharides are polymeric carbohydrates which include sugars, cellulose, starch and glycogen. All the polysaccharides are glycosides in which the acetal carbon atoms of one monosaccharide unit is linked by way of an oxygen to one of the nonacetal carbon atoms of another monosaccharide, such as in:

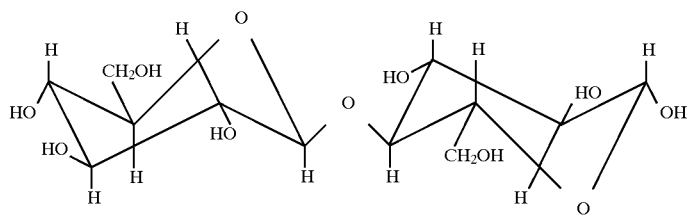

CELLOBIOSE (4-[β-glucosyl]-β-D-glucopyranose)

Sulfated sugar units in polysaccharides include 4-O-substituted D-galactopyranose and 2,6 disulphate residues, such as in carrageenan, which has the structural formula:

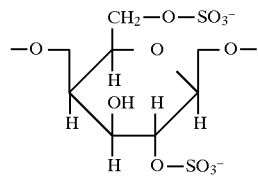

3-O-substituted N-acetyl-D-galactosamine; 4-sulfate residues as in chondroitin sulfate

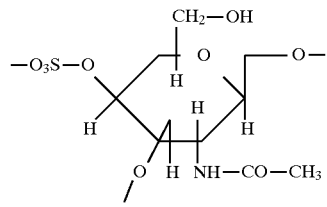

4-O substituted D-glucosamine residues as in heparin

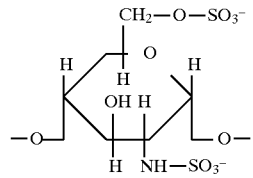

Sulfated esters of polysaccharides having the general formula:

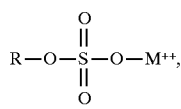

wherein, depending upon the specific polysaccharide, R consists of the following:

| Compound | R |
|---|---|
| kappa carrageenan | 3,6-anhydro-D-galactose linked through C-4 to D-galactose; |
| lambda carrageenan | a-D-galactose units (1AE3) linked; |
| iota carrageenan | D-galactose 3,6-anhydro-D-galactose; |
| Agar—Agar | D-galactose 3,6-anhydro-D-galactose; |
| Furcellaren | D-galactose 3,6-anhydro-D-galactose; |
| Laminaran sulfate | D-glucopyranose units linked through 1 and 3 positions by β-linkages; |
| Galactan sulfate | Galactan; and |
| Chondroitin sulfates | Galactosamino-glucuronans. |

The cation $M^{++}$ can be one of the following or a mixture of the following divalent metal ions: $Mg^{++}$, $Ca^{++}$, $Zn^{++}$, $Ba^{++}$.

B. Carboxylated Polysaccharides

Carboxylated polysaccharides are represented by the general formula

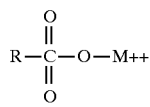

where R is as follows for various compounds:

| Compound | R |
|---|---|
| Pectin | D-galacturonoglycan in which the D-galactopyranosyluronic acid units are connected by (1AE4) glycosidic linkages |
| Algin | anhydro-D-mannuronic acid and anhydro-L-guluronic acid residues |
| Gum karaya | complex polysaccharide; d-galacturonic acid, D-galactose, L-rhamnose |

The cation $M^{++}$ can be one of the following or a mixture of the following divalent metal ions: $Mg^{++}$, $Ca^{++}$, $Zn^{++}$, $Ba^{++}$.

C. Cellulose Derivatives

These polysaccharides are derivatives of the naturally occurring polysaccharide, cellulose. Representative compounds are salts of alkyl cellulose sulfate, salts of acyl cellulose sulfate, and salts of carboxyalkyl cellulose having the following formulas respectively:

$$R'-O-R-O-\overset{O}{\underset{\underset{O}{\|}}{\overset{\|}{S}}}-O-M^{++}$$

$$R'O-\overset{O}{\underset{}{\overset{|}{C}}}-R-O-\overset{O}{\underset{\underset{O}{\|}}{\overset{\|}{S}}}-O-M^{++}$$

$$R-\overset{O}{\overset{\|}{C}}-R''-\overset{O}{\overset{\|}{C}}-O-M^{++}$$

wherein:
R=anhydroglucose residue;
R=$CH_3$; $C_2H_5$; $C_3H_7$;
R"=$CH_3$; $C_2H_5$; and
$M^{++}$=$Ca^{++}$, $Zn^{++}$, $Ba^{++}$, or $Mg^{++}$.
Specific examples of these compounds are:
Sodium ethylcellulose sulfate;
Sodium cellulose acetate sulfate; and
Sodium carboxymethyl cellulose.

D. Sulfated. Sulfonated or Carboxylated Synthetic Polymers

These polymers may have aliphatic or aromatic backbones with sulfonate, sulfate or carboxyl groups attached according to the following general formulas respectively:

$$R-\overset{O}{\underset{\underset{O}{\|}}{\overset{\|}{S}}}-O-M^{++}, \quad R-O-\overset{O}{\underset{\underset{O}{\|}}{\overset{\|}{S}}}-O-M^{++} \quad \text{and}$$

$$R-\overset{O}{\overset{\|}{C}}-O-M^{++}$$

wherein R is an aliphatic or aromatic hydrocarbon chain such as polystyrene, poly(sulfone resin), or carboxylated (poly)vinyl, and $M^{++}$ is $Mg^{++}$, $Ca^{++}$, $Zn^{++}$, $Ba^{++}$.

II. Cationic Polymers

These polymers carry positive charges when in the ionized form. Aminopolysaccharides are representative of this group of polymers. These polymers are mainly of animal origin which contain units of amino sugars, most frequently D-glucosamine (2-amino-2-deoxy-D-galactose).

Representative compounds of this class have the general formula of:

$$R-NH_2, \quad R-NH-\overset{O}{\overset{\|}{C}}-R' \quad \text{and} \quad R-NH-\overset{O}{\underset{\underset{O}{\|}}{\overset{\|}{S}}}-O-M^{++}$$

wherein R is a sugar residue, R' is $CH_3$ or $C_2H_5$, and $M^{++}$ is $Mg^{++}$, $Ca^{++}$, $Zn^{++}$, $Ba^{++}$.

Specific examples of such compounds are: Chondroitin Sulfates which can be characterized as being both anionic and cationic due to the electrostatic charges present, Dermatan Sulfate, Keratosulfate, Hyaluronic Acid, Heparin, and Chitin.

III. Neutral Polymers

Neutral polymers effective in the practice of the present invention are those which include atoms having polarizable electrons, such as oxygen, nitrogen, sulfur, fluoride, chloride, bromide and iodide. In the presence of a cation such as $Ca^{++}$, $Zn^{++}$, $Ba^{++}$ and $Mg^{++}$, these polymers are partially polarized, thus giving rise to the intermolecular interactions between the polymer and the protein molecules of the skin surface.

Representative polymers include:

A. Polysaccharides
 Examples: Starch, Glycogen, Glucan, Fructans, Mannans, Galactomannas, Glucomannas, Galactans, Abrabinans, Xylans, Glycuranans, Guar Gum, Locust Bean Gum, Dextran, Starch Amylose, and Starch Amylopectin.

B. Cellulose Derivatives
 Examples: Methylcellulose, Hydroxyethylcellulose, Ethylhydroxyethyl cellulose and Hydroxypropyl cellulose.

C. Synthetic Polymers
 Examples: Polyvinylpyrrolidone, Polyvinyl alcohol, and Ethylene oxide polymers.

Formulations of the Present Invention

The formulations of the present invention comprise:
(a) of from about 1.0 to about 65% w/w of an anti-hyperalgesic/anti-pruritic compound;
(b) of from about 1 to about 76% w/w of a polymeric material having atoms containing polarizable electrons thereon in combination with a divalent cation in a ratio of from about 7.7 parts to about 1 part or less; and
(c) from about 23 to about 34% w/w of a pharmaceutically acceptable carrier.

The pharmaceutically acceptable carrier is an aqueous carrier in which both the anti-hyperalgesic/anti-pruritic compound and the polymeric material is at least partially water soluble; however compounds and materials which are essentially completely water soluble are preferred. To obtain sufficient solubility the aqueous carrier may contain solvents such as ethanol, t-butanol, hexane and glycol.

Formulations of the present invention can also be prepared in aerosol forms by nebulizing the formulations using a variety of nebulizing techniques known in the art, such as, forming a solution or a suspension of the polymer and the active agent contained therein in a liquid propellant. Both liquid and vapor phases are present in a pressurized container and when the valve of the container is opened, the liquid propellant containing the formulation is released producing and depositing a fine mist onto the site of treatment. The aerosol formulations typically contain of from about 30 to 80% w/w of a propellant, the remaining percentage being the active aqueous formulation. Propellants useful for practicing the invention include chlorinated, fluorinated and chlorofluorated lower molecular weight hydrocarbons, nitrous oxide, carbon dioxide, butane and propane.

Other ingredients, such as preservatives and dyes, may be included in the aqueous carrier of the film-forming composition comprising of from about 0.001 to about 1.5% of the aqueous carrier.

Ingredients which contribute to the healing of the site of injury by preventing infection and accelerating the healing process may also be used in the aqueous carrier of the film-forming composition comprising of from about 0.001 to about 5.0% w/w of the aqueous carrier. Such ingredients are well known to those skilled in the art of healing and include antibacterials, antivirals, antifungals, anti-inflammatories, anesthetics and mixtures thereof These ingredients are described by the various editions of the Physicians Desk Reference (such as PDR, 1993 Edition) and are incorporated herein by reference. Non-limiting, illustrative examples are:

Antibacterial agents, such as Streptomycin, Rifamycin, Ampicillin, Penicillin O, Penicillin V, Bacitracin, Doxycycline, Methacycline, Minocycline, Tetracycline, Acetyl Sulfisoxazole, Succinylsulfathiazole, Sulfaloxic Acid, Sulfapyrazine, and Acetosulfone.

Antifungal agents, such as Dermostatin, Fungichromin, Clotrimazole, Econazole, Potassium Iodide and Propionic Acid.

Anti-inflammatory agents, such as Diclofenac, Tolmetin, Ibuprofen, Protizinic Acid, Glycol Salicylate and Sulfasalazine.

Antiseptic Agents, such as Chlorhexidine, Calcium Iodate, Iodine, Chloroxylenol Hexachlorophene, Boric Acid, and Cupric Sulfate.

Antiviral agents, such as Acyclovir, Trifluridine and Zidovudine.

The following formulation examples illustrate, without limitation, the present invention.

EXAMPLE 1

The formulation is prepared by mixing the ingredients together until the mixture is homogeneous. The pH is adjusted to about 7.0.

|  | Weight % |
| --- | --- |
| Loperamide HCl | 25.0 |
| Sodium Carrageenan | 25.0 |
| Calcium Lactate | 32.0 |
| Q.S. with water to | 100.0 |

EXAMPLE 2

The formulation is prepared by dissolving loperamide HCl in ethanol followed by mixing the other ingredients until the mixture is homogeneous. The pH is adjusted to about 8.0.

|  | Weight % |
| --- | --- |
| Loperamide HCl | 30.0 |
| Ethanol | 20.0 |
| Sodium Ethylcellulose Sulfate | 25.0 |
| Calcium Lactate | 10.0 |
| Q.S. with water to | 100.0 |

In a glass vessel, a suspension of 10% w/w calcium lactate and sodium ethylcellulose sulfate was stirred with an overhead stirrer. The suspension was then warmed to 55°–70° C. and with stirring, a solution of 30% w/w Loperamide HCl in ethanol was added. The mixture was mixed thoroughly at high speed and the pH of the mixture was adjusted to 8.0 with buffers. The mixture was stirred while being cooled to room temperature to provide a homogeneous emulsion containing 30% Loperamide HCI.

EXAMPLE 3

Following the process described in Example 2, a film-forming composition containing 5% w/w Loperamide HCl was prepared.

EXAMPLE 4

Following the process described in Example 2, a film-forming composition containing 60% w/w Loperamide HCl was prepared.

EXAMPLE 5

10% w/w Pectin-NF and 5% w/w calcium lactate in water were stirred thoroughly and warmed to 55°–65° C. A 50% w/w solution of 4-(p-chlorophenyl)-4-hydroxy-N.N-dimthyl-α,α-diphenyl-1-piperidine, N-oxide in ethanol was added to the mixture, agitation was continued, and the pH of the mixture was adjusted to 5.5 and made up to 100% w/w with water. The mixture was cooled to room temperature slowly with a high speed of stirring to ensure the homogeneity of the emulsion. This resulted in a 50% emulsion of 4-(p-chlorophenyl)-4-hydroxy-N,N-dimethyl-α,α-diphenyl-1-piperidone, N-oxide.

|  | Weight % |
| --- | --- |
| 4-(p-chlorophenyl)-4-hydroxy-N-N-dimethyl α,α-diphenyl-1-piperidenebutyramide, N-oxide | 50.0 |
| Ethanol | 10.0 |
| Pectin-NP | 10.0 |
| Calcium Lactate | 5.0 |
| Q.S. with water to | 100.0 |

EXAMPLE 6

Following the process described in Example 5, a film-forming composition containing 5% w/w of 4-(p-chlorophenyl)-4-hydroxy-N,N-dimethyl-α,α-diphenyl-1-piperidine, N-oxide was made.

EXAMPLE 7

Following the process described in Example 5, a film-forming composition containing 60% w/w of 4-(p-chlorophenyl)-4-hydroxy-N,N-dimethyl-α,α-diphenyl-1-piperidine, N-oxide was made.

EXAMPLE 8

30% w/w Polyvinylpyrrolidone and 20% zinc chloride in water were stirred in a container with mechanical stirrer and heated to 55°–65° C. A 15% w/w solution of Loperamide HCl in benzyl alcohol was added and high speed agitation was continued while the mixture was slowly cooled to room temperature. The pH of the mixture was adjusted to 8.5 with a buffer solution and made up to 100% w/w with water. Thus a 15% w/w emulsion of Loperamide HCl was prepared.

|  | Weight % |
| --- | --- |
| Loperamide HCl | 15.0 |
| Benzyl Alcohol | 10.0 |
| Polyvinylpyrrolidone | 30.0 |
| Zinc Chloride | 20.0 |
| Q.S. with water to | 100.0 |

EXAMPLE 9

Following the process described in Example 8, a film-forming composition containing 5% w/w Loperamide HCl was prepared.

EXAMPLE 10

Following the process described in Example 8, a film-forming composition containing 60% w/w Loperamide HCl was prepared.

EXAMPLE 11

The procedure of Example 8 was followed. The pH was adjusted to about 6.5.

|  | Weight % |
| --- | --- |
| Loperamide HCl | 60.0 |
| Starch Amylose | 15.0 |
| Ethanol | 5.0 |
| Calcium Lactate | 10.0 |
| Q.S. with water to | 100.0 |

In preparing the formulations of the present invention the film-forming materials are dissolved in water and the viscosity of the solution is measured using a Brookfield viscometer. Typical viscosities for various film-forming materials are shown in Table I.

TABLE I

| Solution | Viscosity in cps |
| --- | --- |
| 1% Gelcarin-HMR | 200 |
| 3.5% Gelcarin-HMR | 22,000 |
| 6.5% Gelcarin-HMR | 86,000 |
| 1% Gelcarin-DG | 16,000 |
| 2% Gelcarin-DG | 60,000 |
| 2.5% Gelcarin-DG | 86,000 |
| 3% Gelcarin-DG | 141,000 |
| 4% Gelcarin-DG | 230,500 |
| 1% Gelcarin-DG + 1% Ca lactate | 5,000 |
| 3.5% Gelcarin-DG + 3.5% Ca lactate | 48,000 |
| 3.5% Viscarin | 41,000 |
| 3.5% Viscarin $Ba^{++}$ | 38,000 |
| 3.5% Viscarin 3.5% Ca lactate | 42,000 |
| 4% Viscarin | 80,000 |
| 3.5% Viscarin-DG + 3.5% Ca lactate | 76,000 |
| 1% Klucel | 1,200 |
| 2% Klucel | 20,000 |
| 2% Pectin | 280 |
| 3% Pectin | 1,150 |
| 3.5% Pectin | 1,800 |
| 4% Pectin | 4,100 |
| 5% Pectin | 13,500 |
| 3.5% Polystyrene sulfonic acid | 250 |
| 3.5% Starch H-50B | 1,700 |
| 3.5% Starch 36,46:5 | 1,500 |
| 3.5% Chondroitin Sulfate "C" | 50 |

The required amount of the anti-hyperalgesic/anti-pruritic compound is dissolved in an organic solvent, such as ethanol, and added to the solution of the film-forming material Other ingredients, such as preservatives, antibacterials, disinfectants and the like, are then added directly to the solution or, alternatively, may be first dissolved in a suitable solvent prior to their addition to the solution.

The desired viscosities of a formulation may be adjusted by the further addition of solvents, other ingredients such as viscosity increasing and buffering agents and/or water. In so doing, the desired consistency of the formulation can be obtained in the form of a solution, suspension, lotion, paste and cream. These techniques are well-known to those skilled in the art.

In the methods of treatment, a formulation is applied to the site of the inflammed/injured/itchy area by depositing the same thereon in the form of a solution, suspension, lotion, cream, paste or spray-on aerosol and allowing the formulation to form a coating. The active ingredients are then in intimate contact with the site of application, are bioavailable to the underlining skin surface, and effect reduction/elimination of pain or itch without causing CNS side effects.

TESTING OF THE COMPOSITIONS FOR ANTIHYPERALGESIC ACTIVITY

A. Treatment of Abrasions

In separate experiments, two white males, ages 54 and 52, generated a dermal abrasion by folding a piece of 100 grit sandpaper over an index finger or a small block of wood so that a rectangular surface of the sandpaper approximately 50×15 mm or 130×40 mm, respectively, was placed in contact with the skin. The sandpaper was rubbed back and forth a total of 60 times (30 times in each direction) during a period of approximately 30 sec over an area of skin on the inside of the forearm, approximately midway between the wrist and the elbow, of each subject, producing a moderate stinging sensation throughout the process. The treatment produced a reddened abraded area, but no bleeding was observed. The abrading process produced stinging pain in each subject that subsided within an hour or two and was replaced after 8 to 12 hours by hyperalgesia of the abraded area. Hyperalgesia was assessed by tactile stimulation of the affected area, which continued to be red and which also appeared inflamed.

Approximately 12 hours after the abrasion was performed, the abraded area was divided into approximately two equal areas, separated by an area approximately 1 cm wide. To one area was applied approximately 0.2 grams of a placebo formulation and to the other area was applied approximately 0.2 grams of the 5% w/w formulation of Loperamide HCl of Example 3. The 1 cm area separating the two equal areas of application received no treatment. The applications were performed in a "double blind" manner, where a first individual weighed a fixed amount of both the placebo and the Loperamide formulations, coded them by letter, and gave them to a second individual who was unaware of the meaning of the letter coding. Then the second individual applied the formulations to each subject. The subjects were unaware of the meaning of the letter coding of the formulations.

The treated areas were occluded by coverage with gauze bandages. This method of occlusion, coupled with the separation of the two treated areas from the untreated area, effectively prevented the formulations from mixing with each other. Three hours after the formulations were applied, the occlusive coverings were removed, and the two areas were tested for hyperalgesia by tactile and/or thermal stimulation. The subjects were able to distinguish clearly the degree of hyperalgesia in the two areas. When the code was broken, the area that had been selected as having less hyperalgesia was the area which had received the Loperamide formulation.

B. Treatment of Sunburn

A white, 49 year old female subject generated a controlled sunburn on the abdomen. This was accomplished by the placement of two adhesive bandages (2 inch×3 inch) on the subject's abdomen separated by a 1 inch wide area of exposed skin. The long dimension (3 in) of the bandages ran parallel to the longitudinal axis of the body. The exposed abdominal areas, including the 1 in wide area between the two patches, were then liberally covered with a commercial "sun block" formulation and then the excess formulation was removed. This was done in order to block exposure to sun in the entire area except for the two rectangular areas that were protected by the adhesive bandages. The adhesive bandages were then removed and the subject laid on her back with full exposure to the sun for approximately 2 hours.

The two areas which were unprotected by the sun block developed typical sunburn-induced erythema and hyperalgesia. The hyperalgesia was quite pronounced from hour 12 onward. At hour 18, approximately 0.8 grams of placebo formulation of Example 3 D and 0.8 grams of a 5% formulation of 4-(p-chlorophenyl)-4-hydroxy-N,N-dimethyl-α,α-diphenyl-1-piperidine, N-oxide of Example 6, were applied separately to the two hyperalgesic areas. The application was performed in a double blind manner, where a first individual weighed the placebo and 4-(p-chlorophenyl)-4-hydroxy-N,N-dimethyl-α,α-diphenyl-1-piperidine, N-oxide-containing formulations, letter-coded them and gave them to a second individual who did not know the meaning of the codes. The second individual then delivered the coded samples to a third individual who also was unaware of the meaning of the codes. Finally, the formulations were applied to the hyperalgesia abdominal areas of the experimental subject, who also did not know the meaning of the codes. The codes were not broken until 24 hours after the experiment had been completed After the two formulations were applied to the two 2 in×3 in test sites, the test sites were occluded by covering them with separate pieces of plastic wrap and sealing the edges of the plastic wrap with adhesive tape, in order to prevent the formulations from mixing with each other. Three hours after the formulations were applied, the occlusive coverings were removed, and the two areas were tested for the degree of hyperalgesia by tactile stimulation. The experimental subject was able to clearly distinguish the degrees of hyperalgesia in the two adjacent areas. When the code was broken the following day, the area that had been selected as having less hyperalgesia was the area which received the 4-(p-chlorophenyl)-4-hydroxy-N,N-dimethyl-α,α-diphenyl-1-piperidine, N-oxide formulation.

C. Treatment of Frostbite

A frost bite-like condition was generated in a male of Asian origin, age 49, by the placement of a pellet of dry ice of approximately 10 to 15 mm in diameter on the tip of each of two fingers of the right hand of the subject for approximately 30 to 35 seconds. This treatment resulted in the whitening of the skin over an area of approximately 50 mm$^2$, accompanied by stinging sensations and pain.

After approximately 18 to 20 hours, the tips of the fingers were visually red and a stinging pain was produced when light pressure was applied to the reddened areas. One of the fingers was treated with topical application of approximately 0.1 grams of placebo formulation and the other finger was treated with approximately 0.1 grams of a 5% w/w formulation of Loperamide HCl of Example 3. The applications were performed in a double blind manner. A first individual weighed the placebo and Loperamide-containing formulations, letter-coded them and gave them to a second individual who did not know the meaning of the codes. The second person then applied the formulations to the subject, who was also unaware of the meaning of the codes.

The treatment areas were occluded with bandages. After approximately 2 hours of treatment, the subject was able to distinguish clearly the degree of hyperalgesia in the two finger tips, especially when the area was subjected to light pressure. When the code was broken, the finger tip having less hyperalgesia was the one which received the Loperamide formulation.

TESTING OF THE FILM-FORMER COMPOSITIONS FOR ANTI-PRURITIC ACTIVITY

Testing was performed in a mouse scratch model under blind conditions.

Groups of 8–10 male Swiss albino mice (Hilltop Lab Animals, Inc., Scottsdale, Pa.), weighing 2.5–2.6 g, were used in the testing. They were housed under controlled temperature of 23°–25° C. Food and water were freely available. Before the experiments, the mice were weighted, put into individual boxes and allowed to acclimate for 30 min.

Materials

Vehicle used to dissolve the test compounds: 20% w/w cremafor EL.

To induce scratching Compound 48/80 (Sigma, St. Louis, USA) was used which has been shown to produce an itch sensation in humans (Armstrong et al, J. of Physiol., 120: 326, 1953).

The compounds to be tested for anti-pruritic activity were dissolved in the vehicle of 20% w/w cremafor EL.

Method

100 µl of the vehicle (3–5 doses, n=8–10) was injected s.c. into the back of the neck of mice 20 min. before challenging them with 100 µl of Compound 48/80 (2 mg/ml; 50 µg) injected s.c. into the back of the neck. One minute later the mice were observed for 30 min. and the number of hindleg scratching movements directed to the neck was counted.

The vehicle-injected mice scratched 79±16 times in the 30 min after the standard challenge with Compound 48/80.

To each mouse of a group of 8–10 mice previously subjected to the standard challenge various doses of the compounds, to be tested for anti-pruritic activity, were administered s.c. into the back of the neck. One minute later the mice were observed for 30 min and the number of hindleg scratching movements directed to the neck was counted.

For each group of 8–10 mice, the mean values for scratching were no to relative % antagonism of scratching and then plotted vs. dose of test compounds. Interval estimates of mean $A_{50}$ were determined by nonlinear regression analysis (Kaleida Graph) and mean % inhibition of scratching was calculated.

The following compounds were tested:
(1) 1-[3,3-diphenyl-3-(2-pyridyl)propyl]-4-phenyl-4-piperidinecarboxylic acid hydrochloride;
(2) 1-(3,3,3-triphenylpropyl)-4-hydroxy-4-p-chlorobenzylpiperidine; and
(3) 4-(p-chlorophenyl-4-hydroxy-N-N-dimethyl-α,α-diphenylpiperidine-1-butyramide[loperamide].

Each compound (1, 2, 3) antagonized Compound 48/80-induced scratching in a dose-related manner. Results are shown in Table C.

TABLE C

| | Mean % Inhibition of Scratching | |
|---|---|---|
| Compound | Dose (mg/kg, s.c.) | Mean % Inhibition |
| (1) | 2.5 | 32 |
| | 5.0 | 65 |
| | 10.0 | 83 |
| (2) | 1.0 | 35 |
| | 2.5 | 68 |
| | 5.0 | 94 |
| (3) | 0.5 | 18 |
| | 1.0 | 47 |
| | 2.5 | 65 |

Other compounds tested have shown similar anti-pruritic, dose-responsive activity in the range of from about 15 to about 95% based on doses of form about 0.5 to 10.0 mg/kg, s.c.

It should be understood by those skilled in the art that, while the invention has been described and illustrated above in connection with certain specific embodiments, many variations and modifications may be employed without departing from the scope of the invention.

What is claimed is:

1. A method for the prevention or treatment of pruritus in a mammal patient comprising topically administering to said mammalian patient an effective amount of a film-forming composition comprising:

a) of from about 1 to about 65% w/w of an anti-pruritic compound selected from the group consisting of:

2-[4-(4-hydroxy-4-phenylpiperidino)-2,2-diphenylbutyryl]-piperidine;

1-{4-[4-hydroxy-4-(3-triluoromethylphenyl)-piperidino]-2,2-diphenylbutyl}piperidine;

4-(p-chlorophenyl)-4-hydroxy-N-N-,y-trimethyl-α-α-diphenylpiperidine-1-butyramide;

4-(p-chlorophenyl)-4-hydroxy-N-N-dimethyl-α-α-diphenylpiperidine-1-butyramide;

4-(3,4-dichlorophenyl)-N-N-diethyl-4-hydroxy-α-α-diphenylpiperidine-1-butyramide;

4-(3,4-dichlorophenyl)-4-hydroxy-N-N-dimethyl-α-α-diphenylpiperidine-1-butyramide 4-(4-chloro-3-trifluoromethylphenyl)-4-hydroxy-N-N-dimethyl-α-α-diphenylpiperidine 1-butyramide;

4-(p-fluorophenyl)-4-hydroxy-N-N-,y-trimethyl-α-α-diphenylpiperidine-1-butyramide;

4-(p-bromophenyl)-4-hydroxy-N-N-dimethyl-α-α-diphenylpiperidine-1-butyramide;

4-(p-chlorophenyl)-N-ethyl-4-hydroxy-N-methyl-α-α-diphenylpiperidine-1-butyramide;

1-(3,3,3-triphenylpropyl)-4-phenyl-4-piperidinecarboxylic acid hydrochloride;

ethyl 1-(3,3,3-triphenylpropyl)-4-phenyl-4-piperidinecarboxylate;

potassium 1-(3,3,3-triphenylpropyl)-4-phenyl-4-piperidinecarboxylate;

sodium 1-(3,3,3-triphenylpropyl)-4-phenyl-4-piperidinecarboxylate;

1-[3,3-diphenyl-3-(2-pyridyl)propyl]-4-phenyl-4-piperidinecarboxylic acid hydrochloride;

sodium 1-[3,3-diphenyl-3-(2-pyridyl)propyl]-4-phenyl-4-piperidinecarboxylate;

ethyl 1-[3,3-diphenyl-3-(2-pyridyl)propyl]-4-phenyl-4-piperidinecarboxylate;

potassium 1-[3,3-diphenyl-3-(2-pyridyl)propyl]-4-phenyl-4-piperidinecarboxylate;

1-(3,3,3-triphenylpropyl)-4-phenyl-4-piperidinemethanol;

1-[3,3-diphenyl-3-(2-pyridyl)propyl-4-phenyl-4-piperidinemethanol;

1-(3,3,3-triphenylpropyl)-4-phenyl-4-acetoxymethyl-piperidine;

1-(3,3,3-triphenylpropyl)-4-phenyl-4-methoxymethyl-piperidine;

1-(3,3,3-triphenylpropyl)-4-(4-chlorophenyl)-4-piperidinemethanol;

1-[3-(p-chlorophenyl)-3,3-diphenylpropyl]-4-(phenyl)-4-piperidinemethanol;

1-[3-(p-tolyl)-3,3-diphenylpropyl]-4-(phenyl)-4-piperidinemethanol;

1-[3-(p-bromophenyl)-3,3-diphenylpropyl]-4-(phenyl)-4-piperidinemethanol;

1-[3,3-diphenyl-3-(4-pyridyl)-propyl]-4-phenyl-4-piperidinemethanol;

1-[3,3-diphenyl-3-(3-pyridyl)propyl]-4-phenyl-4-piperidinemethanol;

1-(3,3,3-triphenylpropyl)-4-phenyl-4-hexoxymethyl-piperidine;

1-(3,3,3-triphenylpropyl)-4-(p-tolyl)-4-piperidinemethanol;

1-(3,3,3-triphenylpropyl)-4-(p-trifluoromethyl)-4-piperidinemethanol;

1-(3,3,3-triphenylbutyl)-4-(phenyl)-4-piperidinemethanol;

1-(3,3,3-triphenylpropyl)-4-(phenyl)-4-piperidinemethanol;

1-(3,3,3-triphenylpropyl)-4-(phenyl)-4-methoxyethylpiperidine;

1-[3,3-diphenyl-3-(2-pyridyl)propyl]-4-phenyl-4-methoxyethylpiperidine;

1-(3,3,3-triphenylpropyl)-4-phenyl-4-piperidinemethanol;

1-[3,3-diphenyl-3-(2-pyridyl)propyl]-4-phenyl-4-piperidinemethanol;

1-(3,3,3-triphenylpropyl)-4-phenyl-4-acetoxymethylpiperidine;

1-(3,3,3-triphenylpropyl)-4-phenyl-4-methoxymethylpiperidine;

1-(3,3,3-triphenylpropyl)-4-(chlorophenyl)-4-piperidinemethanol;

1-(3,3,3-triphenylpropyl)-4-hydroxy-4-benzylpiperidine;

1-(3,3,3-triphenylpropyl)-4-hydroxy-4-benzylpiperidine hydrochloride;

1-(3,3,3-triphenylpropyl)-4-hydroxy-4-p-chlorobenzylpiperidine;

1-(3,3,3-triphenylpropyl)-4-hydroxy-4-p-methylbenzylpiperidine; and

1-[3,3,3-(2-pyridyl)propyl]-4-benzyl-4-hydroxypiperidine.

said anti-pruritic compound incorporated in a film-forming material, said anti-pruritic compound being devoid of central nervous system side effects when topically delivered to the mammalian patient;

b) said film-forming polymeric material being present in said composition of from about 1 to about 76% w/w and is capable of forming an essentially continuous film in the pH environment of about 5.5 to 8.5, said polymeric material having atoms containing polarizable electrons thereon, said atoms being selected from the group consisting of oxygen, nitrogen, sulfur, in combination with a divalent cation, said divalent cation selected from the group consisting of $CA^{++}$, $MG^{++}$, $Zn^{++}$ and $Ba^{++}$, wherein the ratio of said atoms containing the polarizable electrons to said divalent catons is in the range of from about 7.7 to about 1, said film-forming material selected from the group consisting of sodium ethylcellulose sulfate,
sodium cellulose acetate sulfate,
sodium carboxymethyl cellulose,
chondroitin sulfate,
dermatan sulfate,
keratosulfate,
hyaluronic acid,
heparin and
chitin,
and c) of from about 23 to about 34% w/w of an aqueous pharmaceutically acceptable carrier comprising a solvent selected from the group consisting of ethanol, t-butanol, hexane, glycol and benzyl alcohol in admixture with water, wherein said film-forming composition is in the form of a solution, suspension, lotion, cream, spray or aerosol.

* * * * *